United States Patent
Hamm et al.

(10) Patent No.: US 7,101,394 B2
(45) Date of Patent: Sep. 5, 2006

(54) ENERGETICALLY-CONTROLLED DELIVERY OF BIOLOGICALLY ACTIVE MATERIAL FROM AN IMPLANTED MEDICAL DEVICE

(75) Inventors: Mark A Hamm, Lynnfield, MA (US); Louis J Barbato, Franklin, MA (US); Robert J Crowley, Sudbury, MA (US); Wendy Naimark, Cambridge, MA (US); Hatal Patel, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 99 days.

(21) Appl. No.: 10/428,768

(22) Filed: May 2, 2003

(65) Prior Publication Data
US 2004/0030379 A1 Feb. 12, 2004

Related U.S. Application Data

(60) Provisional application No. 60/377,428, filed on May 2, 2002.

(51) Int. Cl.
*A61F 2/06* (2006.01)
*A61F 2/00* (2006.01)
(52) U.S. Cl. .................. 623/1.42; 623/1.44; 623/23.73; 623/23.75; 424/424; 424/426
(58) Field of Classification Search ...... 623/1.42–1.46, 623/23.73, 23.75, 23.76; 424/424–426
See application file for complete search history.

(56) References Cited

U.S. PATENT DOCUMENTS

| 4,882,167 | A | 11/1989 | Jang |
| 5,817,017 | A | 10/1998 | Young et al. |
| 5,919,126 | A | 7/1999 | Armini |
| 2001/0000802 | A1 | 5/2001 | Soykan et al. |
| 2002/0082685 | A1 | 6/2002 | Sirhan et al. |
| 2002/0115986 | A1 | 8/2002 | Shadduck |
| 2002/0128704 | A1 | 9/2002 | Daum et al. |
| 2002/0138154 | A1 | 9/2002 | Li et al. |
| 2003/0004563 | A1 | 1/2003 | Jackson et al. |
| 2003/0050692 | A1 | 3/2003 | Sirhan et al. |

*Primary Examiner*—Bruce Snow
(74) *Attorney, Agent, or Firm*—Jones Day

(57) ABSTRACT

A medical device and system capable of providing on-demand delivery of biologically active material to a body lumen patient, and a method of making such medical device. A first coating layer comprising a biologically active material and optionally a polymeric material is disposed on the surface of the medical device. A second coating layer comprising magnetic particles and a polymeric material is disposed on the first coating layer. The second coating layer, which is substantially free of a biologically active material, protects the biologically active material prior to delivery. The system includes the medical device and a source of energy, such as an electromagnetic or mechanical vibrational energy. When the patient is exposed to the energy source, the magnetic particles move out of the second coating layer and create channels therein through which the biologically active material can be released.

4 Claims, 13 Drawing Sheets

ENERGETICALLY-CONTROLLED DELIVERY OF BIOLOGICALLY ACTIVE MATERIAL FROM AN IMPLANTED MEDICAL DEVICE

RELATED APPLICATION

The present invention claims the benefit of U.S. Provisional Application No. 60/377,428, filed May 2, 2002.

FIELD OF THE INVENTION

The present invention generally relates to medical devices capable of providing on-demand delivery of biologically active material to a patient. In particular, the invention is directed to medical devices comprising a biologically active material, which is released from the device when the biologically active material is needed by the patient. The biologically active material is released when the patient is exposed to an energy source, such as electromagnetic energy or mechanical vibrational energy. When electromagnetic energy is used the medical device should also comprise magnetic particles that facilitate the release of the biologically active material.

BACKGROUND OF THE INVENTION

In order to treat a variety of medical conditions, insertable or implantable medical devices having a coating for release of a biologically active material have been used. For example, various types of drug-coated stents have been used for localized delivery of drugs to a body lumen. See U.S. Pat. No. 6,099,562 to Ding et al. Such stents have been used to prevent, inter alia, the occurrence of restenosis after balloon angioplasty. However, delivery of the biologically active material to the body tissue immediately after insertion or implantation of the stent may not be needed or desired. For instance, it may be more desirable to wait until restenosis occurs or begins to occur in a body lumen that has been stented with a drug-coated stent before the drug is released. Therefore, there is a need for implantable medical devices that can provide on-demand delivery of biologically active materials when such materials are required by the patient after implantation of the medical device. Also needed is a non-invasive method to facilitate or modulate the delivery of the biologically active material from the medical device after implantation.

SUMMARY OF THE INVENTION

These and other objectives are accomplished by the present invention. To achieve these objectives, we have invented an insertable medical device that permits on-demand delivery of a biologically active material from the medical device when it is implanted in a patient. The release of the biologically active material is modulated and/or facilitated by the application of an extracorporal or external energy source, such as an electromagnetic energy source or a mechanical vibrational energy source. More specifically, the medical device, that is insertable into the body of a patient, comprises a surface and a first coating layer disposed on at least a portion of the surface. The first coating layer comprises a biologically active material. A second coating layer is disposed over the first coating layer and comprises magnetic particles and a polymeric material. The second coating layer is substantially free of the biologically active material, and preferably free of any biologically active material. When the patient is exposed to an extracorporal electromagnetic energy source, the release of the biologically active material from the coated medical device is facilitated. In this way, the biologically active material can be delivered to the patient only when he or she requires such material.

In order to further achieve the aforementioned objectives, also described herein is a system for providing on-demand delivery of a biologically active material to a patient. This system comprises an insertable medical device that comprises a surface and a first coating layer disposed on at least a portion of the surface. The first coating layer comprises a biologically active material. A second coating layer is disposed over the first coating layer and comprises magnetic particles and a polymeric material. The second coating layer is substantially free of the biologically active material, and preferably free of any biologically active material. The system also comprises an electromagnetic energy source or mechanical vibrational energy source for facilitating the delivery of the biologically active material when the patient is exposed to this energy source.

Another embodiment of the invention is a method for a making a medical device for delivering a biologically active material to a patient. The method comprises providing a medical device that is insertable into the body of the patient and comprises a surface. The method further comprises disposing a first coating layer comprising a biologically active material on at least a portion of the surface of the medical device. A second coating layer comprising a polymeric material and magnetic particles is disposed on the first coating layer. The second coating layer is substantially free of the biologically active material, and preferably free of any biologically active material.

The present medical device of the present invention can provide a desired release profile of a biologically active material. The desired release profile can be achieved because the medical device is coated with a first coating layer comprising a biologically active material and a second coating layer comprising magnetic particles that overlies or covers the first coating layer. The second coating layer is substantially free of a biologically active material so that the biologically active material is not exposed and is protected during implantation and prior to release into the body lumen of a patient. Because the second coating layer is substantially free of any biologically active material, there can be a higher concentration of magnetic particles in the second coating layer than if there were a biologically active material in the second coating layer. In addition, when the magnetic particles in the second coating layer are exposed to an energy source and move out of the second layer, the biologically active material is not immediately released. Instead, there is a controlled release of the biologically active material because the biologically active material migrates from the first coating layer and through the second coating layer before being delivered to a body lumen of a patient.

DETAILED DESCRIPTION OF THE INVENTION

A. Drug Release Modulation Employing an Electromagnetic Energy Source

Figure 1:
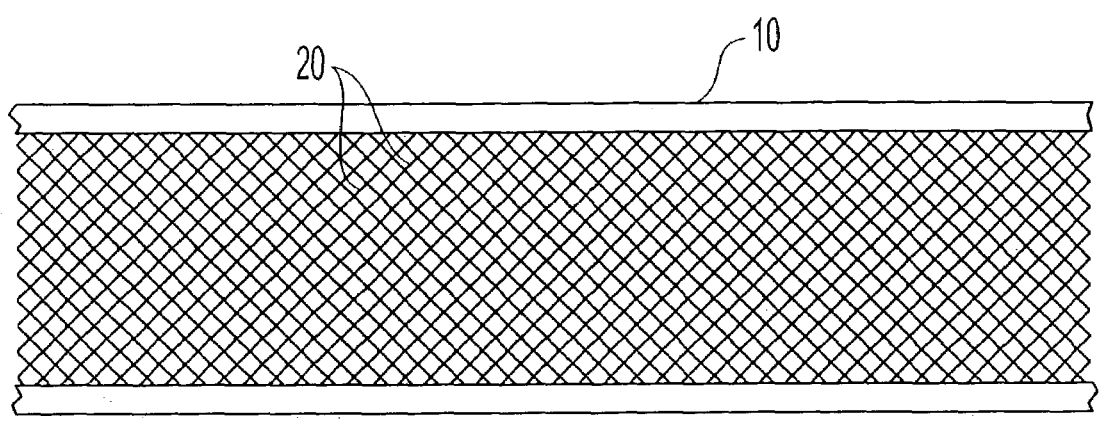
FIG. 1 is a cross-sectional view of a stent 10 comprising wire-like struts 20.

The system of the present invention comprises (1) a medical device having a coating containing a biologically active material, and (2) a source of electromagnetic energy or a source for generating an electromagnetic field. The present invention can facilitate and/or modulate the delivery of the biologically active material from the medical device. The release of the biologically active material from the medical device is facilitated or modulated by the electromagnetic energy source or field. To utilize the system of the present invention, the practitioner may implant the coated medical device using regular procedures. After implantation, the patient is exposed to an extracorporal or external electromagnetic energy source or field to facilitate the release of the biologically active material from the medical device. The delivery of the biologically active material is on-demand, i.e., the material is not delivered or released from the medical device until a practitioner determines that the patient is in need of the biologically active material. The coating of the medical device of the present invention further comprises particles comprising a magnetic material, i.e., magnetic particles. An example of the medical device of the present invention is illustrated in FIG. 1. The medical device is a stent 10 which is comprised of wire-like coated struts 20.

Figure 2A:
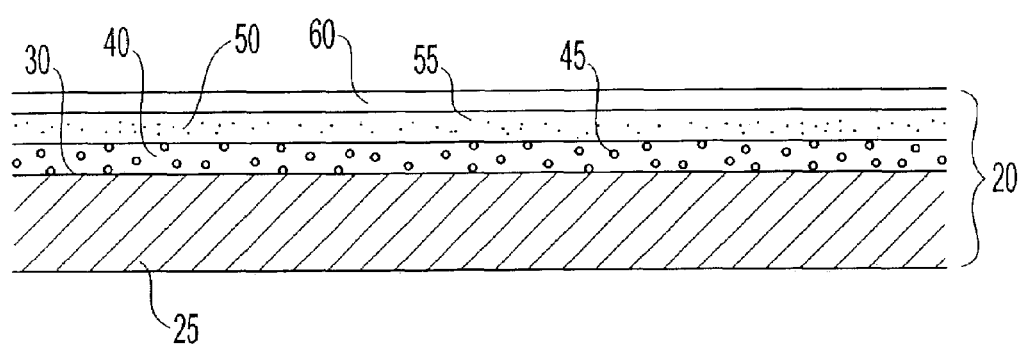
FIG. 2A is a cross-sectional view of a coated strut 20 of a stent as shown in FIG. 1. The coated strut comprises a strut 25 and a surface 30 covered with a coating.
Figure 2B:
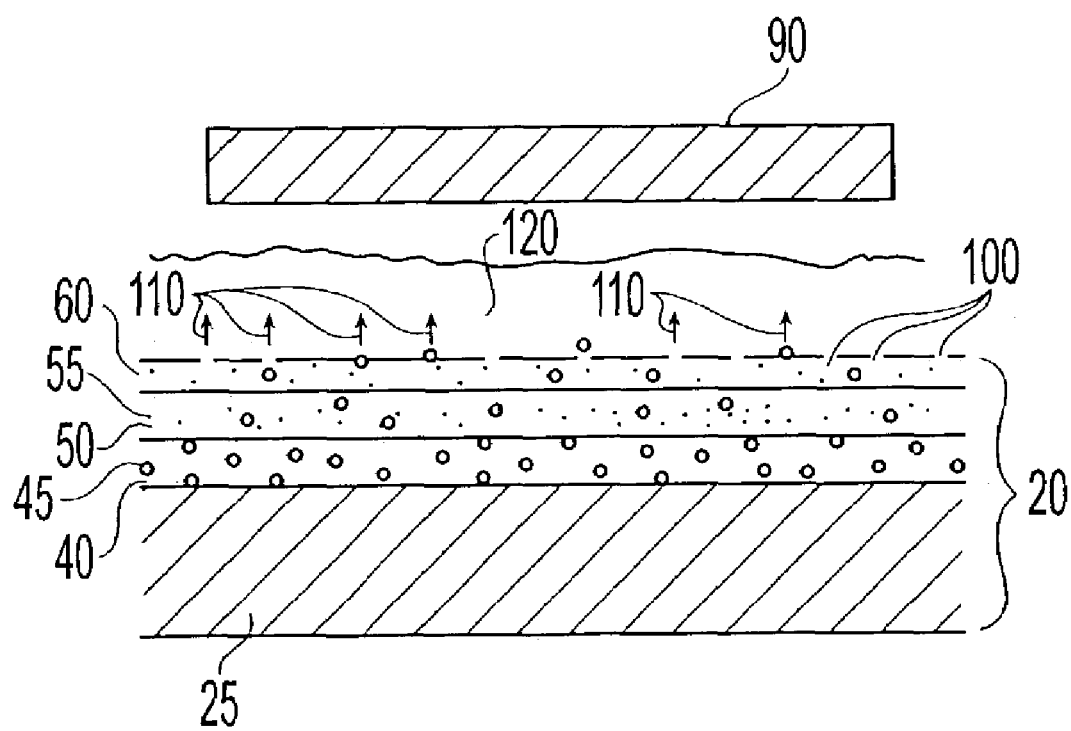
FIG. 2B shows the effect on the coated strut of FIG. 2A when the patient is exposed to an electromagnetic field 90.

An embodiment of the medical device of the present invention is illustrated in FIG. 2A. FIG. 2A shows a cross-sectional view of a coated strut of a stent. The coated strut 20 comprises a strut 25 having a surface 30. The coated strut 20 has a coating that comprises a first coating layer 40 that contains a biologically active material 45. Preferably, this coating layer also contains a polymeric material. A second coating layer 50 comprising magnetic particles 55 is disposed over the first coating layer 40. This second coating layer can also include a polymeric material. A third coating layer or sealing layer 60 is disposed on top of the second coating layer 50. FIG. 2B illustrates the effect of exposing a patient, who is implanted with a stent having struts shown in FIG. 2A, to an electromagnetic energy source or field 90. When such a field is applied, the magnetic particles 55 move out of the second coating layer 50 as shown by the upward arrow 110. This movement disrupts the sealing layer 60 and forms channels 100 in the sealing layer 60. The size of the channels 100 formed generally depends on the size of the magnetic particles 55 used. The biologically active material 45 can then be released from the coating through the disrupted sealing layer 60 into the surrounding tissue 120. The duration of exposure to the field and the strength of the electromagnetic field 90 determine the rate of delivery of the biologically active material 45.

Figure 3A:
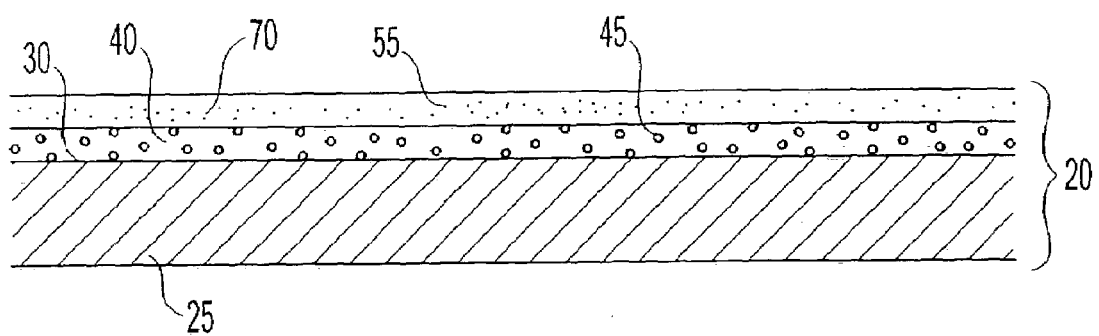
FIG. 3A is a cross-sectional view of a portion of a coated strut 20 of a stent.
Figure 3B:
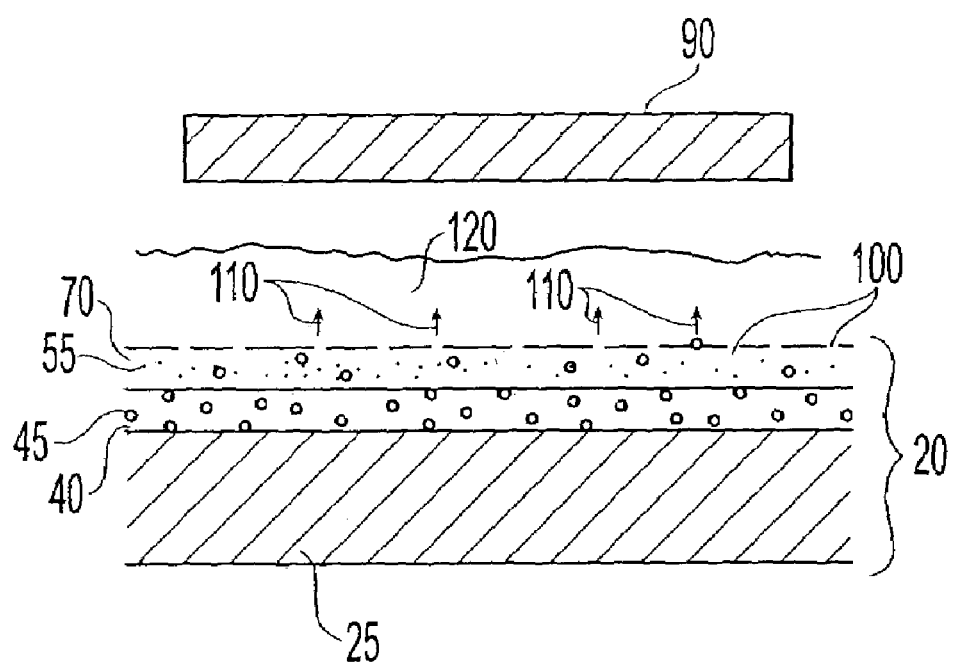
FIG. 3B shows the effect on the strut of FIG. 3A when the patient is exposed to an electromagnetic field 90.

FIG. 3A shows another specific embodiment of a coated stent strut 20. The coating comprises a first coating layer 40 comprising a biologically active material 45 and preferably a polymeric material disposed over the surface 30 of the strut 25. A second coating layer or sealing layer 70 comprising magnetic particles 55 and a polymeric material is disposed on top of the first coating layer 40. FIG. 3B illustrates the effect of exposing a patient who is implanted with a stent having struts shown in FIG. 3A, to an electromagnetic field 90. When such a field is applied, the magnetic particles 55 move through the sealing layer 70 as shown by the upward arrow 110 and created channels 100 in the sealing layer 70. The biologically active material 45 in the underlying first coating layer 40 is allowed to travel through the channels 100 in the sealing layer 70 and be released to the surrounding tissue 120. Since the biologically active material 45 is in a separate first coating layer 40 and must migrate through the second coating layer or the sealing layer 70, the release of the biologically active material 45 is controlled after formation of the channels 100.

Figure 4A:
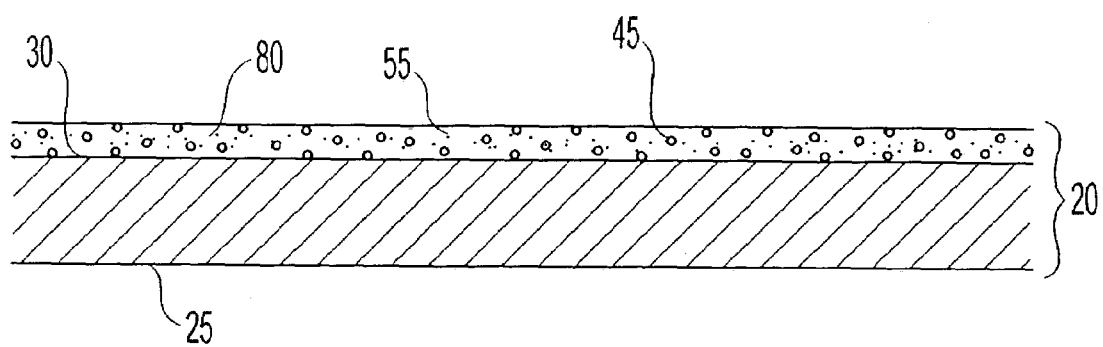
FIG. 4A is a cross-sectional view of a coated strut 20 of a stent.
Figure 4B:
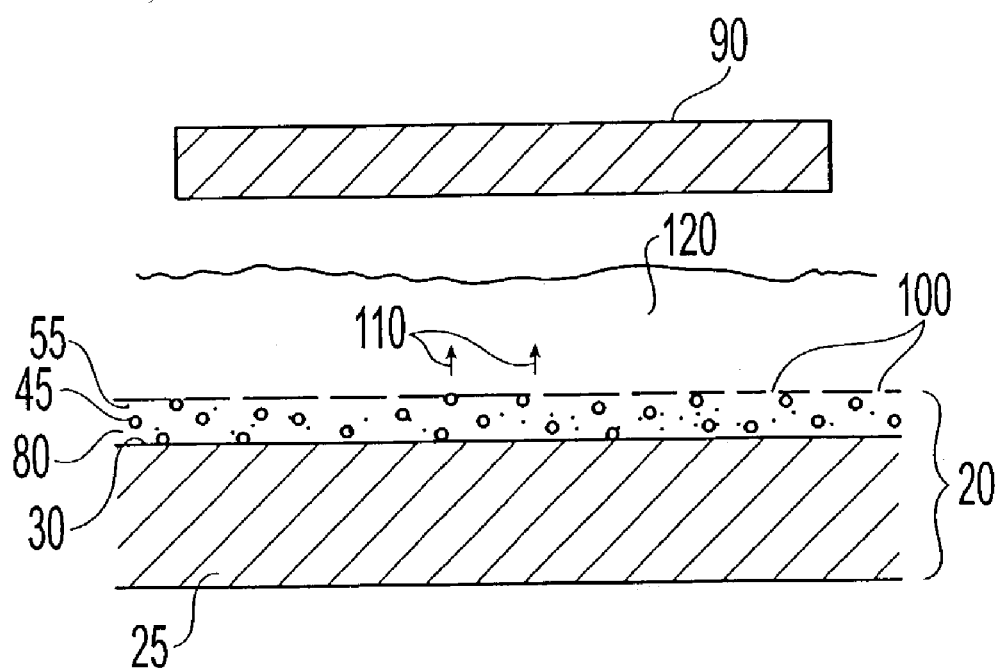
FIG. 4B shows the effect on the strut of FIG. 4A when the patient is exposed to an electromagnetic field 90.

FIG. 4A shows another embodiment of a coated stent strut. The coating comprises a coating layer 80 comprising a biologically active material 45, magnetic particles 55 and a polymeric material. FIG. 4B illustrates the effect of exposing a patient, who is implanted with a stent having struts shown in FIG. 4A to an electromagnetic field 90. The field is applied, the magnetic particles 55 move through the layer 80 as shown by the arrow 110 and create channels in the coating layer 80. The biologically active material 45 can then be released to the surrounding tissue 120.

Figure 5:
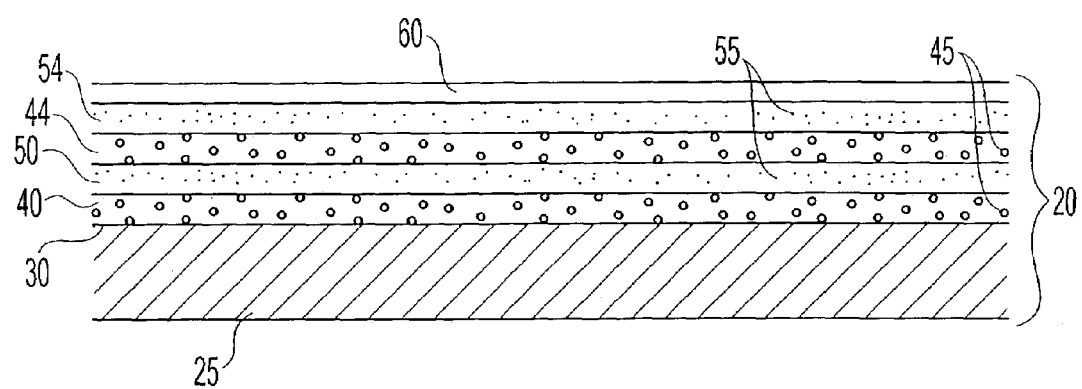
FIG. 5 is a cross-sectional view of a coated strut 20.

In another embodiment, the medical device of the present invention may be a stent having struts coated with a coating comprising more than one coating layer containing a magnetic material. FIG. 5 illustrates such a coated strut 20. The coating comprises a first coating layer 40 containing a polymeric material and a biologically active material 45 which is disposed on the surface 30 of a strut 25. A second coating layer 50 comprising a polymeric material and magnetic particles 55 is disposed over the first coating layer 40. A third coating layer 44 comprising a polymeric material and a biologically active material 45 is disposed over the second coating layer 50. A fourth coating layer 54 comprising a polymeric material and magnetic particles 55 is disposed over this third layer 44. Finally a sealing layer 60 of a polymeric material is disposed over the fourth coating layer 54. The permeability of the coating layers may be different from layer to layer so that the release of the biologically active material from each layer can differ. Also, the magnetic susceptibility of the magnetic particles may differ from layer to layer. The magnetic susceptibility may be varied using different concentrations or percentages of magnetic particles in the coating layers. The magnetic susceptibility of the magnetic particles may also be varied by changing the size and type of material used for the magnetic particles. When the magnetic susceptibility of the magnetic particles differs from layer to layer, different excitation intensity and/or frequency are required to activate the magnetic particles in each layer.

Furthermore, the magnetic particles can be coated with a biologically active material and then incorporated into a coating for the medical device. In a preferred embodiment, the biologically active material is a nucleic acid molecule. The nucleic acid coated magnetic particles may be formed by painting, dipping, or spraying the magnetic particles with a solution comprising the nucleic acid. The nucleic acid molecules may adhere to the magnetic particles via adsorption. Also the nucleic acid molecules may be linked to the magnetic particles chemically, via linking agents, covalent bonds, or chemical groups that have affinity for charged molecules. Application of an external electromagnetic field can cause the adhesion between the biologically active material and the magnetic particle to break, thereby allowing for release of the biologically active material.

In another specific embodiment, the magnetic particles may be molded into or coated onto a non-metallic medical device, including a bio-absorb able medical device. The magnetic properties of the magnetic particles allow the non-metallic implant to be extracorporally imaged, vibrated, or moved. In specific embodiments, the magnetic particles are painted, dipped or sprayed onto the outer surface of the device. The magnetic particles may also be suspended in a curable coating, such as a UV curable epoxy, or they may be electrostatically sprayed onto the medical device and subsequently coated with a UV or heat curable polymeric material.

Furthermore, in certain embodiments, the movement of the magnetic particles that occurs when the patient implanted with the coated device is exposed to an external electromagnetic field, can release mechanical energy into the surrounding tissue in which the medical device is implanted and trigger histamine production by the surrounding tissues. The histamine has a protective effect in preventing the formation of scar tissues in the vicinity at which the medical device is implanted.

Also the application of the external electromagnetic field can activate the biologically active material in the coating of the medical device. A biologically active material that may be used in this embodiment may be a thermally sensitive substance that is coupled to nitric oxide, e.g., nitric oxide adducts, which prevent and/or treat Adverse effects associated with use of a medical device in a patient, such as restenosis and damaged blood vessel surface. The nitric oxide is attached to a carrier molecule and suspended in the polymer of the coating, but it is only biologically active after a bond breaks releasing the smaller nitric oxide molecule in the polymer and eluting into the surrounding tissue. Typical nitric oxide adducts include nitroglycerin, sodium nitroprusside, S-nitroso-proteins, S-nitroso-thiols, long carbon-chain lipophilic S-nitrosothiols, S-nitrosodithiols, iron-nitrosyl compounds, thionitrates, thionitrites, sydnonimines, furoxans, organic nitrates, and nitrosated amino acids, preferably mono- or poly-nitrosylated proteins, particularly polynitrosated albumin or polymers or aggregates thereof. The albumin is preferably human or bovine, including humanized bovine serum albumin. Such nitric oxide adducts are disclosed in U.S. Pat. No. 6,087,479 to Stamler et al. which is incorporated herein by reference.

Moreover, the application of electromagnetic field may effect a chemical change in the polymer coating thereby allowing for faster release of the biologically active material from the coating.

B. Drug Release Modulation Employing a Mechanical Vibrational Energy Source

Another embodiment of the present invention is a system for delivering a biologically active material to a body of a patient that comprises a mechanical vibrational energy source and an insertable medical device comprising a coating containing the biologically active material. The coating can optionally contain magnetic particles. After the device is implanted in a patient, the biologically active material can be delivered to the patient on-demand or when the material is needed by the patient. To deliver the biologically active material, the patient is exposed to an extracorporal or external mechanical vibrational energy source. The mechanical vibrational energy source includes various sources which cause vibration such as sonic or ultrasonic energy. Exposure to such energy source causes disruption in the coating that allows for the biologically active material to be released from the coating and delivered to body tissue.

Moreover, in certain embodiments, the biologically active material contained in the coating of the medical device is in a modified form. The modified biologically active material has a chemical moiety bound to the biologically active material. The chemical bond between the moiety and the biologically active material is broken by the mechanical vibrational energy. Since the biologically active material is generally smaller than the modified biologically active material, it is more easily released from the coating. Examples of such modified biologically active materials include the nitric oxide adducts described above.

In another embodiment, the coating comprises at least a coating layer containing a polymeric material whose structural properties are changed by mechanical vibrational energy. Such change facilitates release of the biologically active material which is contained in the same coating layer or another coating layer.

C. Materials Suitable for the Invention

1. Suitable Medical Devices

The medical devices of the present invention are insertable into the body of a patient. Namely, at least a portion of such medical devices may be temporarily inserted into or semi-permanently or permanently implanted in the body of a patient. Preferably, the medical devices of the present invention comprise a tubular portion which is insertable into the body of a patient. The tubular portion of the medical device need not to be completely cylindrical. For instance, the cross-section of the tubular portion can be any shape, such as rectangle, a triangle, etc., not just a circle.

The medical devices suitable for the present invention include, but are not limited to, stents, surgical staples, catheters, such as central venous catheters and arterial catheters, guidewires, balloons, filters (e.g., vena cava filters), cannulas, cardiac pacemaker leads or lead tips, cardiac defibrillator leads or lead tips, implantable vascular access ports, stent grafts, vascular grafts or other grafts, interluminal paving system, intra-aortic balloon pumps, heart valves, cardiovascular sutures, total artificial hearts and ventricular assist pumps.

Medical devices which are particularly suitable for the present invention include any kind of stent for medical purposes, which are known to the skilled artisan. Suitable stents include, for example, vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 4,733,665 issued to Palmaz, U.S. Pat. No. 4,800,882 issued to Gianturco, U.S. Pat. No. 4,886,062 issued to Wiktor and U.S. Pat. No. 5,449,373 issued to Pinchasik et al. A bifurcated stent is also included among the medical devices suitable for the present invention.

The medical devices suitable for the present invention may be fabricated from polymeric and/or metallic materials. Examples of such polymeric materials include polyurethane and its copolymers, silicone and its copolymers, ethylene vinyl-acetate, poly(ethylene terephthalate), thermoplastic elastomer, polyvinyl chloride, polyolephines, cellulosics, polyamides, polyesters, polysulfones, polytetrafluoroethylenes, acrylonitrile butadiene styrene copolymers, acrylics, polyactic acid, polyclycolic acid, polycaprolactone, polyacetal, poly(lactic acid), polylactic acid-polyethylene oxide copolymers, polycarbonate cellulose, collagen and chitins. Examples of suitable metallic materials include metals and alloys based on titanium (e.g., nitinol, nickel titanium alloys, thermo-memory alloy materials), stainless steel, platinum, tantalum, nickel-chrome, certain cobalt alloys including cobalt-chromium-nickel alloys (e.g., Elgiloy® and Phynox®) and gold/platinum alloy. Metallic materials also include clad composite filaments, such as those disclosed in WO 94/16646.

2. Magnetic Particles

In the instant specification, the term "magnetic particles" means particles comprising a magnetic material. Magnetic materials include ferromagnetic substances, i.e., substances which exhibit good magnetic susceptibility, such as ferrous substance including iron oxide steel, stainless steel; paramagnetic substances, such as aluminum, which have unpaired electrons and are attracted into a magnetic field; diamagnetic substances, such as gold, wherein all electrons are paired and are slightly repelled by the electromagnetic field. Preferably, the magnetic particles used for the present invention comprise a ferromagnetic substance. However, magnetic particles comprising paramagnetic or diamagnetic substances are particularly useful for imaging the medical device in a patient's body, for example, using magnetic resonance imaging ("MRI") because the strong magnetic field in MRI would not negatively affect the particles but would enable or enhance the ability of MRI to detect them.

The magnetic particles may be capsules made of nonmagnetic substance, such as silica, encapsulating a magnetic substance or particles made of a mixture of a nonmagnetic substance and a magnetic substance. Also, the magnetic particles may be coated with a polymeric material to reduce any undesirable effects that may be caused by the corrosive nature of the magnetic substance. In another embodiment, ferrous loaded polymers are incorporated into the coating instead of magnetic particles. Examples of the ferrous loaded polymers include iron dextran.

The average size of the particles is normally within the range from about 0.01 µm to about 10 µm. However, the average particle size may be any other suitable range such as from about 0.01 µm to about 50 µm. The sizes should be determined based on various factors including a thickness of the coating layer in which the particles are contained or by which the particles are covered, and desired release rate of the biologically active material. Also, when the biologically active material to be released from the medical device has comparatively greater size, i.e., cells or other large size genetic materials, the magnetic particles of greater size should be chosen. Suitable particles are not limited to any particular shape.

Magnetic particles useful for the present invention, such as magnetic iron oxide particles (mean particle diameter 200 nm, density 5.35 g/cm$^3$ and magnetization 30 emu/g) and magnetic silica particles, Sicaster-M™ (mean particle diameter 800–1500 nm, density 2.5 g/cm$^3$ and magnetization ~4.0 emu/g) are commercially available, for example, from Micromod Partikeltechnologie.

The concentration of the magnetic particles in a coating should be determined based on various factors including the size of the particles and desired release rate of the biologically active material. Normally, the concentration of the magnetic particles in a coating ranges from about 2% to about 20%.

3. Biologically Active Material

The term "biologically active material" encompasses therapeutic agents, such as drugs, and also genetic materials and biological materials. The genetic materials mean DNA or RNA, including, without limitation, of DNA/RNA encoding a useful protein stated below, anti-sense DNA/RNA, intended to be inserted into a human body including viral vectors and non-viral vectors. Examples of DNA suitable for the present invention include DNA encoding anti-sense RNA tRNA or rRNA to replace defective or deficient endogenous molecules angiogenic factors including growth factors, such as acidic and basic fibroblast growth factors, vascular endothelial growth factor, epidermal growth factor, transforming growth factor α and β, platelet-derived endothelial growth factor, plateletderived growth factor, tumor necrosis factor α, hepatocyte growth factor and insulin like growth factor cell cycle inhibitors including CD inhibitors thymidine kinase ("TK") and other agents useful for interfering with cell proliferation, and the family of bone morphogenic proteins ("BMP's") as explained below. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Non-viral vectors include artificial chromosomes and minichromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD).

The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor α and β, platelet derived endothelial growth factor, platelet derived growth factor, tumor necrosis factor α, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. Alternatively or in addition, molecules capable of inducing an upstream or downstream effect of a BMP can be provided. Such molecules include any of the "hedgehog" proteins, or the DNA's encoding them. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Biologically active material also includes non-genetic therapeutic agents, such as:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, and acetylsalicylic acid, amlodipine and doxazosin;

anti-inflammatory agents such as glucocorticoids, betamethasone, dexamethasone, prednisolone, corticosterone, budesonide, estrogen, sulfasalazine, and mesalamine;

immunosuppressants such as sirolimus (RAPAMYCIN), tacrolimus, everolimus and dexamethasone, antineoplastic/antiproliferative/anti-miotic agents such as paclitaxel, 5-fluorouracil, cisplatin, vinblastine, vincristine, epothilones, methotrexate, azathioprine, halofuginone, adriamycin, actinomycin and mutamycin; cladribine; endostatin, angiostatin and thymidine kinase inhibitors, and its analogs or derivatives;

anesthetic agents such as lidocaine, bupivacaine, and ropivacaine;

anti-coagulants such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;

vascular cell growth promotors such as growth factors, Vascular Endothelial Growth Factors (FEGF, all types including VEGF-2), growth factor receptors, transcriptional activators, and translational promotors;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

Also, the biologically active materials of the present invention include trans-retinoic acid and nitric oxide adducts. A biologically active material may be encapsulated in micro-capsules by the known methods.

4. Coating Compositions

The coating compositions suitable for the present invention can be applied by any method to a surface of a medical device to form a coating. Examples of such methods are painting, spraying, dipping, rolling, electrostatic deposition and all modern chemical ways of immobilization of biomolecules to surfaces.

The coating composition used in the present invention may be a solution or a suspension of a polymeric material and/or a biologically active material and/or magnetic particles in an aqueous or organic solvent suitable for the medical device which is known to the skilled artisan. A slurry, wherein the solid portion of the suspension is comparatively large, can also be used as a coating composition for the present invention. Such coating composition may be applied to a surface, and the solvent may be evaporated, and optionally heat or ultraviolet (UV) cured.

The solvents used to prepare coating compositions include ones which can dissolve the polymeric material into solution and do not alter or adversely impact the therapeutic properties of the biologically active material employed. For example, useful solvents for silicone include tetrahydrofuran (THF), chloroform, toluene, acetone, isooctane, 1,1,1-trichloroethane, dichloromethane, and mixture thereof.

A coating of a medical device of the present invention may consist of various combinations of coating layers. For example, the first layer disposed over the surface of the medical device can contain a polymeric material and a first biologically active material. The second coating layer, that is disposed over the first coating layer, contains magnetic particles and optionally a polymeric material. The second coating layer protects the biologically active material in the first coating layer from exposure during implantation and prior to delivery. Preferably, the second coating layer is substantially free of a biologically active material.

Another layer, i.e. sealing layer, which is free of magnetic particles, can be provided over the second coating layer. Further, there may be another coating layer containing a second biologically active material disposed over the second coating layer. The first and second biologically active materials may be identical or different. When the first and second biologically active material are identical, the concentration in each layer may be different. The layer containing the second biologically active material may be covered with yet another coating layer containing magnetic particles. The magnetic particles in two different layers may have an identical or a different average particle size and/or an identical or a different concentrations. The average particle size and concentration can be varied to obtain a desired release profile of the biologically active material. In addition, the skilled artisan can choose other combinations of those coating layers.

Alternatively, the coating of a medical device of the present invention may comprise a layer containing both a biologically active material and magnetic particles. For example, the first coating layer may contain the biologically active material and magnetic particles, and the second coating layer may contain magnetic particles and be substantially free of a biologically active material. In such embodiment, the average particle size of the magnetic particles in the first coating layer may be different than the average particle size of the magnetic particles in the second coating layer. In addition, the concentration of the magnetic particles in the first coating layer may be different than the concentration of the magnetic particles in the second coating layer. Also, the magnetic susceptibility of the magnetic particles in the first coating layer may be different than the magnetic susceptibility of the magnetic particles in the second coating layer.

The polymeric material should be a material that is biocompatible and avoids irritation to body tissue. Examples of the polymeric materials used in the coating composition of the present invention include, but not limited to, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate, styrene-isobutylene copolymers and blends and copolymers thereof. Also, other examples of such polymers include polyurethane (BAYHDROL®, etc.) fibrin, collagen and derivatives thereof, polysaccharides such as celluloses, starches, dextrans, alginates and derivatives, hyaluronic acid, and squalene. Further examples of the polymeric materials used in the coating composition of the present invention include other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (etylene-propylene-diene) rubbers, fluorosilicones, polyethylene glycol, polysaccharides, phospholipids, and combinations of the foregoing. Preferred is polyacrylic acid, available as HYDROPLUS® (Boston Scientific Corporation, Natick, Mass.), and described in U.S. Pat. No. 5,091,205, the disclosure of which is hereby incorporated herein by reference. In a most preferred embodiment of the invention, the polymer is a copolymer of polylactic acid and polycaprolactone.

More preferably for medical devices which undergo mechanical challenges, e.g. expansion and contraction, the polymeric materials should be selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating composition adheres better to the surface of the medical device when the device is subjected to forces, stress or mechanical challenge.

The amount of the polymeric material present in the coatings can vary based on the application for the medical device. One skilled in the art is aware of how to determine the desired amount and type of polymeric material used in the coating. For example, the polymeric material in the first coating layer may be the same as or different than the polymeric material in the second coating layer. The thickness of the coating is not limited, but generally ranges from about 25 μm to about 0.5 mm. Preferably, the thickness is about 30 μm to 100 μm.

5. Electromagnetic Sources

An external electromagnetic source or field may be applied to the patient having an implanted coated medical device using any method known to skilled artisan. In the method of the present invention, the electromagnetic field is oscillated. Examples of devices which can be used for applying an electromagnetic field include a magnetic resonance imaging ("MRI") apparatus. Generally, the magnetic field strength suitable is within the range of about 0.50 to about 5 Tesla (Webber per square meter). The duration of the application may be determined based on various factors including the strength of the magnetic field, the magnetic substance contained in the magnetic particles, the size of the particles, the material and thickness of the coating, the location of the particles within the coating, and desired releasing rate of the biologically active material.

In an MRI system, an electromagnetic field is uniformly applied to an object under inspection. At the same time, a gradient magnetic field, superposing the electromagnetic field, is applied to the same. With the application of these electromagnetic fields, the object is applied with a selective excitation pulse of an electromagnetic wave with a resonance frequency which corresponds to the electromagnetic field of a specific atomic nucleus. As a result, a magnetic resonance (MR) is selectively excited. A signal generated is detected as an MR signal. See U.S. Pat. No. 4,115,730 to Mansfield, U.S. Pat. No. 4,297,637 to Crooks et al., and U.S. Pat. No. 4,845,430 to Nakagayashi. For the present invention, among the functions of the MRI apparatus, the function to create an electromagnetic field is useful for the present invention. The implanted medical device of the present can be located as usually done for MRI imaging, and then an electromagnetic field is created by the MRI apparatus to facilitate release of the biologically active material. The duration of the procedure depends on many factors, including the desired releasing rate and the location of the inserted medical device. One skilled in the art can determine the proper cycle of the electromagnetic field, proper intensity of the electromagnetic field, and time to be applied in each specific case based on experiments using an animal as a model.

In addition, one skilled in the art can determine the excitation source frequency of the elecromagnetic energy source. For example, the electromagnetic field can have an excitation source frequency in the range of about 1 Hertz to about 300 kiloHertz. Also, the shape of the frequency can be of different types. For example, the frequency can be in the form of a square pulse, ramp, sawtooth, sine, triangle, or complex. Also, each form can have a varying duty cycle.

6. Mechanical Vibrational Energy Source

The mechanical vibrational energy source includes various sources which cause vibration such as ultrasound energy. Examples of suitable ultrasound energy are disclosed in U.S. Pat. No. 6,001,069 to Tachibana et al. and U.S. Pat. No. 5,725,494 to Brisken, PCT publications WO00/16704, WO00/18468, WO00/00095, WO00/07508 and WO99/33391, which are all incorporated herein by reference. Strength and duration of the mechanical vibrational energy of the application may be determined based on various factors including the biologically active material contained in the coating, the thickness of the coating, structure of the coating and desired releasing rate of the biologically active material.

Various methods and devices may be used in connection with the present invention. For example, U.S. Pat. No. 5,895,356 discloses a probe for transurethrally applying focused ultrasound energy to produce hyperthermal and thermotherapeutic effect in diseased tissue. U.S. Pat. No. 5,873,828 discloses a device having an ultrasonic vibrator with either a microwave or radio frequency probe. U.S. Pat. No. 6,056,735 discloses an ultrasonic treating device having a probe connected to a ultrasonic transducer and a holding means to clamp a tissue. Any of those methods and devices can be adapted for use in the method of the present invention.

Ultrasound energy application can be conducted percutaneously through small skin incisions. An ultrasonic vibrator or probe can be inserted into a subject's body through a body lumen, such as blood vessels, bronchus, urethral tract, digestive tract, and vagina. However, an ultrasound probe can be appropriately modified, as known in the art, for subcutaneous application. The probe can be positioned closely to an outer surface of the patient body proximal to the inserted medical device.

The duration of the procedure depends on many factors, including the desired releasing rate and the location of the inserted medical device. The procedure may be performed in a surgical suite where the patient can be monitored by imaging equipment. Also, a plurality of probes can be used simultaneously. One skilled in the art can determine the proper cycle of the ultrasound, proper intensity of the ultrasound, and time to be applied in each specific case based on experiments using an animal as a model.

In addition, one skilled in the art can determine the excitation source frequency of the mechanical vibrational energy source. For example, the mechanical vibrational energy source can have an excitation source frequency in the range of about 1 Hertz to about 300 kiloHertz. Also, the shape of the frequency can be of different types. For example, the frequency can be in the form of a square pulse, ramp, sawtooth, sine, triangle, or complex. Also, each form can have a varying duty cycle.

D. Treatment of Body Tissue with the Invention

The present invention provides a method of treatment to reduce or prevent the degree of restenosis or hyperplasia after vascular intervention such as angioplasty, stenting, atherectomy and grafting. All forms of vascular intervention are contemplated by the invention, including, those for treating diseases of the cardiovascular and renal system. Such vascular intervention include renal angioplasty, percutaneous coronary intervention (PCI), percutaneous transluminal coronary angioplasty (PTCA); carotid percutaneous transluminal angioplasty (PTA); coronary by-pass grafting, angioplasty with stent implantation, peripheral percutaneous transluminal intervention of the iliac, femoral or popliteal arteries, carotid and cranial vessels, surgical intervention using impregnated artificial grafts and the like. Furthermore, the system described in the present invention can be used for treating vessel walls, portal and hepatic veins, esophagus, intestine, ureters, urethra, intracerebrally, lumen, conduits, channels, canals, vessels, cavities, bile ducts, or any other duct or passageway in the human body, either in-born, built in or artificially made. It is understood that the present invention has application for both human and veterinary use.

The present invention also provides a method of treatment of diseases and disorders involving cell overproliferation, cell migration, and enlargement. Diseases and disorders involving cell overproliferation that can be treated or prevented include but are not limited to malignancies, premalignant conditions (e.g., hyperplasia, metaplasia, dysplasia), benign tumors, hyperproliferative disorders, benign dysproliferative disorders, etc. that may or may not result from medical intervention. For a review of such disorders, see Fishman et al., 1985, *Medicine*, 2d Ed., J. B. Lippincott Co., Philadelphia.

Whether a particular treatment of the invention is effective to treat restenosis or hyperplasia of a body lumen can be determined by any method known in the art, for example but not limited to, those methods described in this section. The safety and efficiency of the proposed method of treatment of a body lumen may be tested in the course of systematic medical and biological assays on animals, toxicological analyses for acute and systemic toxicity, histological studies and functional examinations, and clinical evaluation of patients having a variety of indications for restenosis or hyperplasia in a body lumen.

The efficacy of the method of the present invention may be tested in appropriate animal models, and in human clinical trials, by any method known in the art. For example, the animal or human subject may be evaluated for any indicator of restenosis or hyperplasia in a body lumen that the method of the present invention is intended to treat. The efficacy of the method of the present invention for treatment of restenosis or hyperplasia can be assessed by measuring the size of a body lumen in the animal model or human subject at suitable time intervals before, during, or after treatment. Any change or absence of change in the size of the body lumen can be identified and correlated with the effect of the treatment on the subject. The size of the body lumen can be determined by any method known in the art, for example, but not limited to, angiography, ultrasound, fluoroscopy, magnetic resonance imaging, optical coherence tumography and histology.

EXAMPLES

Example 1

To determine the effect of an electromagnetic field on a coated stent with a biologically active material, 15 mm long Nygene PVC tubes with outer circumferences of 11 mm were chosen to model a coronary stent. This model was chosen because it is approximately the size of a coronary stent but has much greater surface area on which to load a biologically active material and minimum magnetic properties. The tubes were coated by a coating composition comprising a biologically active material, polymer and particles of a magnetic material. The biologically active material used in the coating was dexamethasone fluorescein (DMF), which has a molecular weight of 840.98 and is hydrophobic. DMF comprises dexamethasone tagged with a fluoroisothiocyanate (FITC) molecule that has an absorbance wavelength of 490 nm and an excitation wavelength of 520 nm. Iron oxide particles were used as the magnetic material particles. These particles had a mean particle diameter of 200 nm and a density of 5.35 g/cm$^3$. The iron oxide particles also had a magnetization of 30 emu/g.

Since the iron oxide particles, which were obtained from Micromed Partikeltechnologie, are suspended in water, an appropriate amount of the suspension was pipetted into a vial and the water was evaporated off at 37° C. A coating composition composed of 0.3% of DMF, 0.5% of a polymer, 0.2% iron oxide particles and 99% of the solvent tetrahydrofuran (THF) was prepared. This composition was sonicated for 5 minutes to disperse the iron oxide particles into the organic solvent. The composition was stable for approximately 2 minutes, which was sufficient for coating the PVC tubes. The PVC tubes were coated by completely immersing them in the coating composition and then agitating them for about 30 seconds. The PVC tubes were then air-dried for a minimum of 20 minutes. This process was repeated to create a second coat. Coated PVC tubes coated with about 350 μg to about 550 μg coating material were obtained.

Figure 6:
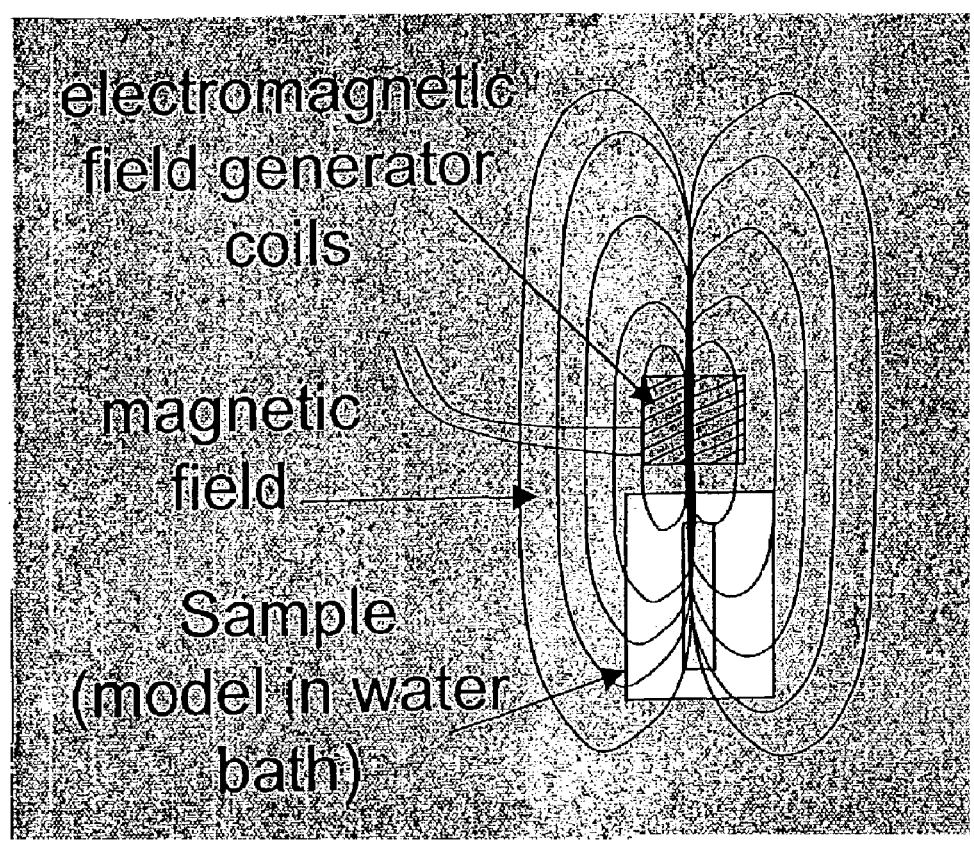
FIG. 6 shows an experimental set-up for determining the effect of exposure to an electromagnetic field on a medical device coated with a coating containing a biologically active material.
Figure 7:
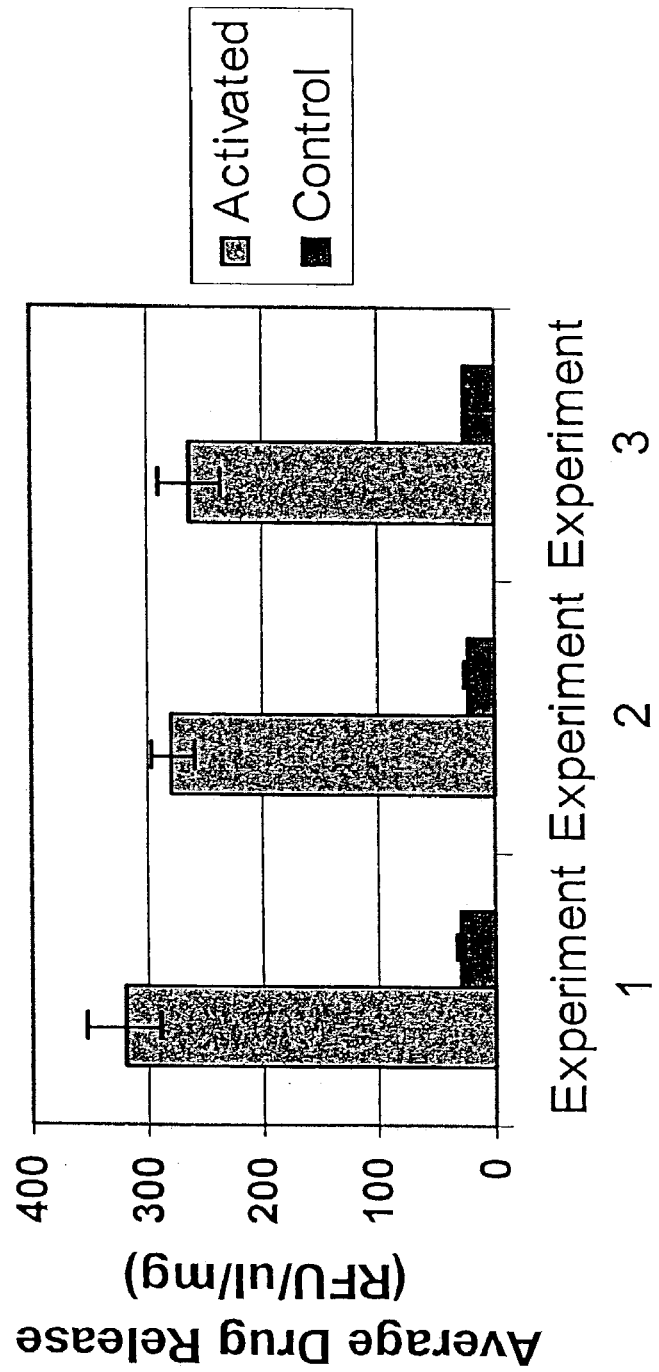
FIG. 7 is a graph showing the effect of exposing a coated medical device to an electromagnetic field.

The coated tubes were immersed in 1.5 mL deionized water baths and positioned under electromagnetic field generator coils, as shown in FIG. 6. The electromagnetic field was pulsed at 150 Hz for 10 sec/minute for 30 minutes. As controls, certain of the coated tubes were immersed in deionized water baths without exposure to an electromagnetic field. Immediately after exposure to the electromagnetic field, samples of the water from the baths containing the coated tubes exposed to the electromagnetic field and the controls were aliquoted into a plate-reader and analyzed by the SPECTRAmax® Microplate Spectrofluorometer to determine the amount of DMF released into the baths. The amount of DMF released is measured in terms of Random fluorescence unit (RFU) per μL/mg DMF. FIG. 7 shows RFU/μL/mg, normalized for the quantity of water sampled for fluorescence and coating weight variations, with standard deviation bars for three (3) measurements of DMF released from the coated tubes under an electromagnetic field. This figure shows that application of the electromagnetic field to the coated tubes increases the release of the DMF as compared to the controls.

Example 2

To determine the minimum magnetic property that the coating needs to have for release rate facilitation to occur release under an electromagnetic field, the procedure of Example 1 was repeated. However, the concentrations of magnetic particles in the coating was varied to find a threshold level of magnetic property that a coating should have to facilitate DMF release from the coating under an electromagnetic field. Each coating composition contained 0.5% of a polymer and 99% of the solvent tetrahydrofuran (THF), and the percentages of the iron oxide particles and DMF were varied; the percentage of the iron oxide particles were reduced to 20%, 10% and 2%, while the percentage of DMF was increased accordingly.

Figure 8:
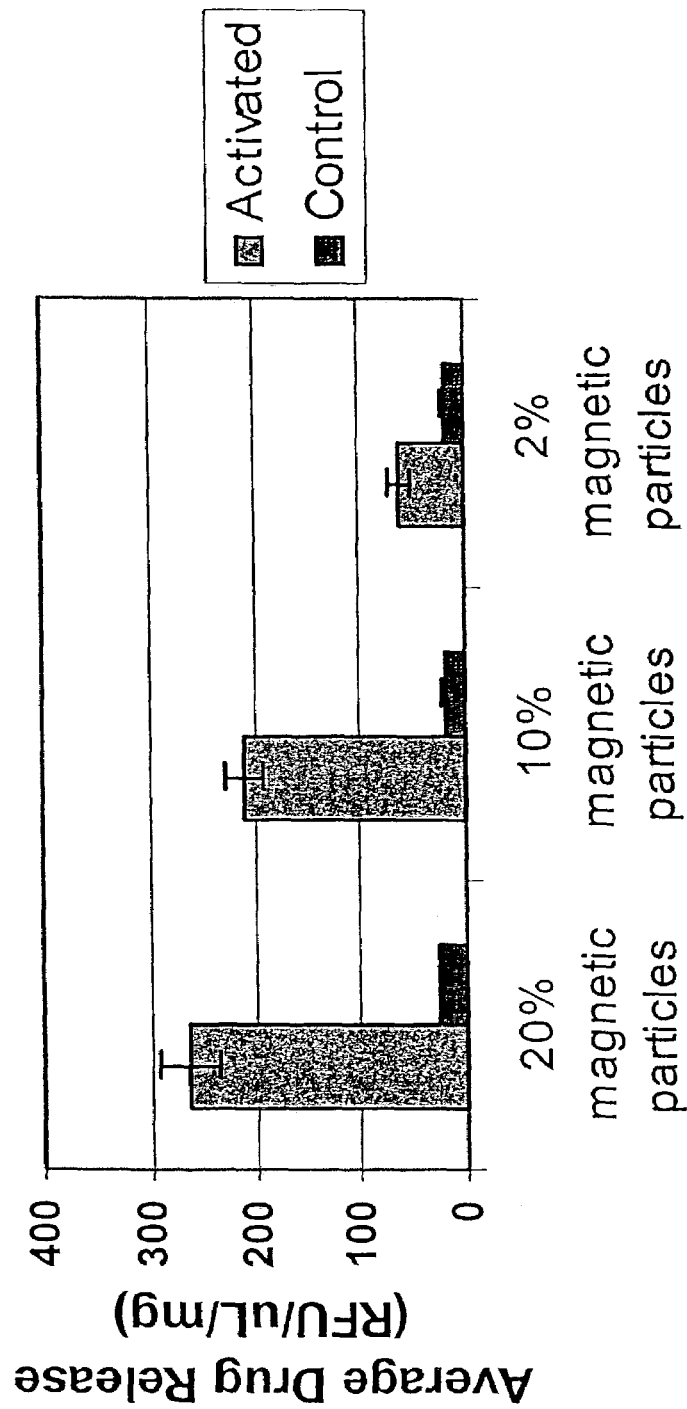
FIG. 8 is a graph showing the effect of exposing a coated medial device to an electromagnetic field when the concentration of magnetic particles in the coating is varied.

The amount of DMF released is measured in terms of Random fluorescence unit (RFU) per μL/mg DMF by an identical manner as in Example 1. FIG. 8 shows RFU/μL/mg values for different concentrations of the magnetic particles. This figure shows that the coating containing from 2% to 20% of iron oxide particles facilitate the release of DMF under the electromagnetic field.

Example 3

To determine the effect of mechanical vibrational energy on a coronary stent coated with a biologically active material, 15 mm long Nygene PVC tubes with outer circumferences of 11 mm were chosen to model a coronary stent. A coating composition composed of 0.3% of DMF, 0.7% of a polymer and 99% of THF was prepared. The PVC tubes were dip-coated in the coating composition. The coated tubes were coupled to a stack actuator with a UV cured epoxy at one of their ends.

Figure 9:
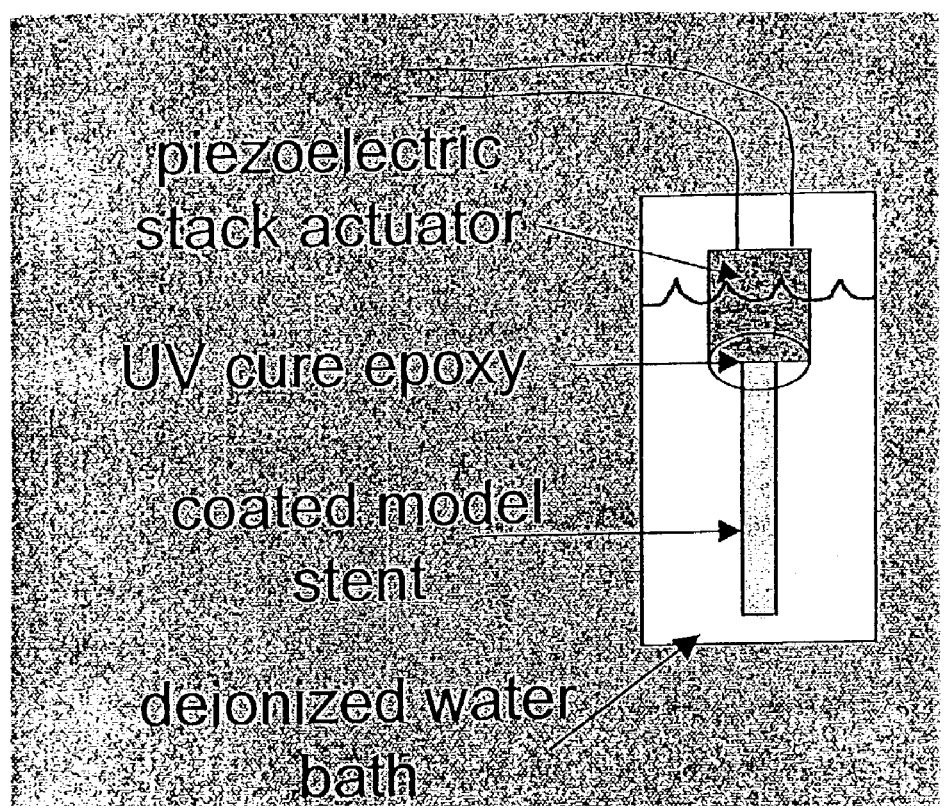
FIG. 9 shows an experimental set-up for determining the effect of exposing a coated medical device to mechanical vibrational energy generated by a stack actuator.
Figure 10:
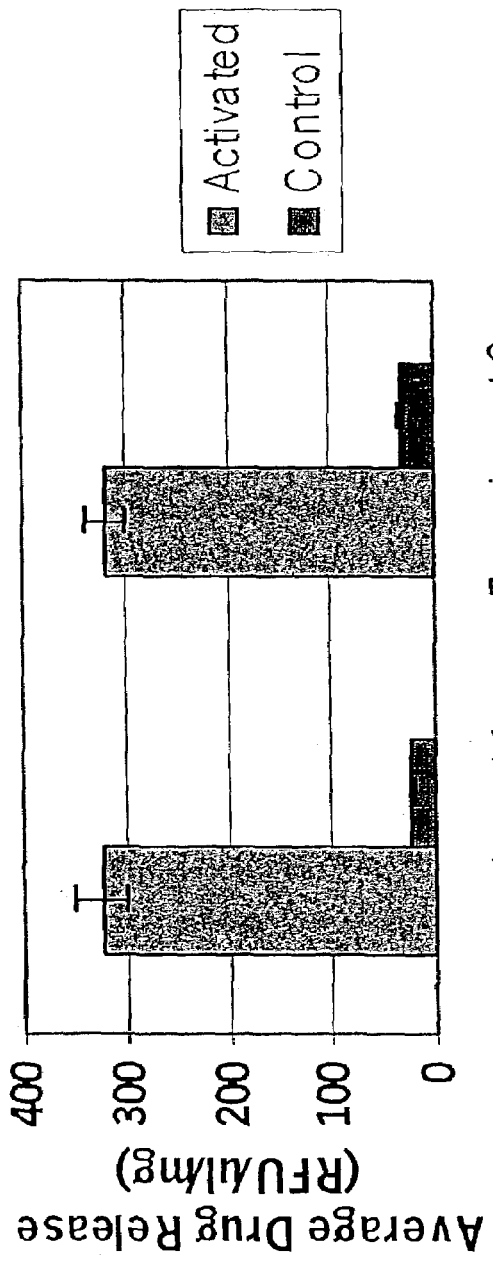
FIG. 10 is a graph showing the effect of exposing a coated medical device to mechanical vibration energy.

The coupled tubes were immersed in 1.5 mL deionized water baths, as shown in FIG. 9. The stack actuator was supplied with a sinusoidal signal at approximately 74.5 kHz for 30 minutes at 20V. The input frequency was selected based on results showing that the natural frequency of a coronary stent is about 74.5 kHz. As controls, certain of the coated tubes were immersed in deionized water baths without being coupled with stack actuator. Samples of the water from the baths containing the tubes exposed to the mechanical vibrational energy and the controls were analyzed with a spectrofluorimeter to determine the amount of DMF released into the baths. The results were scaled to account for volume of water tested and actual amount of DMF in the coating of the tubes (to account for variation in coating weight). The results were shown in FIG. 10. This figure shows that application of the mechanical vibrational energy to the coated tubes increased the release of the DMF as compared to the controls.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

We claim:

1. A medical device that is insertable into the body of a patient comprising:
   (a) a surface;
   (b) a first coating layer comprising a biologically active material and magnetic particles disposed on at least a portion of the surface; and
   (c) a second coating layer comprising a polymeric material and magnetic particles disposed on the first coating layer, wherein the second coating layer is substantially free of the biologically active material, and wherein the average particle size of the magnetic particles in the first coating layer is different than the average particle size of the magnetic particles in the second coating layer.

2. A medical device that is insertable into the body of a patient comprising:
   (a) a surface;
   (b) a first coating layer comprising a biologically active material and magnetic particles disposed on at least a portion of the surface; and
   (c) a second coating layer comprising a polymeric material and magnetic particles disposed on the first coating layer, wherein the second coating layer is substantially free of the biologically active material, and wherein the concentration of the magnetic particles in the first coating layer is different than the concentration of the magnetic particles in the second coating layer.

3. A method for making the medical device of claim 2 comprising:
   (a) providing a medical device that is insertable into the body of the patient which comprises a surface;
   (b) disposing a first coating layer comprising a biologically active material and magnetic particles on at least a portion of the surface; and
   (c) disposing a second coating layer comprising a polymeric material and plurality of magnetic particles on the first coating layer, wherein the second coating layer is substantially free of the biologically active material.

4. A method for making a medical device for delivering a biologically active material to a patient comprising:
   (a) providing a medical device that is insertable into the body of the patient which comprises a surface;

(b) disposing a first coating layer comprising a biologically active material and magnetic particles on at least a portion of the surface; and
(c) disposing a second coating layer comprising a polymeric material and plurality of magnetic particles on the first coating layer, wherein the second coating layer is substantially free of the biologically active material, and wherein the magnetic susceptibility of the magnetic particles in the first coating layer is different than the magnetic susceptibility of the magnetic particles in the second coating layer.

* * * * *